United States Patent [19]

Kung et al.

[11] Patent Number: 4,803,262

[45] Date of Patent: * Feb. 7, 1989

[54] HYBRID CELL LINE FOR PRODUCING MONOCLONAL ANTIBODY TO HUMAN CYTOTOXIC AND SUPPRESSOR T CELLS, ANTIBODY, AND METHODS

[75] Inventors: Patrick C. Kung, Bridgewater; Gideon Goldstein, Short Hills, both of N.J.

[73] Assignee: Ortho Pharmaceutical Corporation, Raritan, N.J.

[*] Notice: The portion of the term of this patent subsequent to Dec. 21, 1999 has been disclaimed.

[21] Appl. No.: 935,167

[22] Filed: Nov. 26, 1986

Related U.S. Application Data

[60] Continuation of Ser. No. 643,593, Aug. 23, 1984, abandoned, which is a division of Ser. No. 432,455, Oct. 4, 1982, Pat. No. 4,637,983, which is a division of Ser. No. 82,515, Oct. 9, 1979, Pat. No. 4,364,932.

[51] Int. Cl.$^4$ .................... A61K 39/395; C07K 15/02
[52] U.S. Cl. .................... 530/387; 530/809; 935/104
[58] Field of Search ............ 435/68, 240, 241, 172.2, 435/948; 436/548; 424/85; 530/387; 935/104, 110

[56] References Cited

U.S. PATENT DOCUMENTS 4,364,932 12/1982 Kung et al. .................... 935/104

OTHER PUBLICATIONS

McMichael et al., "A Human Thymocyte Antigen Defined by a Hybrid Myeloma Monoclonal Antibody" European J. of Immunology, vol. 9, pp. 205–210 (1979).

Ledbetter, "Human Leu T–Cell Differentiation Antigens" Recent Monographs in Immunology, vol. 3, Turk Ed. (1981), pp. 16–22.

Evans, "Thymus–Dependent Membrane Antigens in Man: Inhibition of Cell Mediated Lympholysis by Monoclonal Antibodies" Proc. Natl. Acad. Sci., 78(1), pp. 544–548 (1981)

Reinherz et al., "Monoclonal Antibody Reactive with Human Cytotoxic/Suppressor T–Cell Subset" Journal of Immunology, 124(3), pp. 1301–1307 (1980).

Primary Examiner—John E. Tarcza

[57] ABSTRACT

Hybrid cell line for production of monoclonal antibody to an antigen found on normal human cytotoxic and suppressor T cells. The hybrid is formed by fusing splenocytes from immunized CAF$_1$ mice with P3X63Ag8U1 myeloma cells. Diagnostic and therapeutic uses of the monoclonal antibody are also disclosed.

4 Claims, 2 Drawing Sheets

HYBRID CELL LINE FOR PRODUCING MONOCLONAL ANTIBODY TO HUMAN CYTOTOXIC AND SUPPRESSOR T CELLS, ANTIBODY, AND METHODS

This is a continuation of application Ser. No. 643,593 filed Aug. 23, 1984, abandoned which is a division of our copending application Ser. No. 432,455, filed Oct. 4, 1982, now U.S. Pat. No. 4,637,983 which in turn is a division of application Ser. No. 82,515, filed Oct. 9, 1979, now U.S. Pat. No. 4,364,932.

FIELD OF THE INVENTION

This invention relates generally to new hybrid cell lines and more specifically to hybrid cell lines for production of monoclonal antibody to an antigen found on normal human cytotoxic and suppressor T cells, to the antibody so produced, and to therapeutic and diagnostic methods and compositions employing this antibody.

DESCRIPTION OF THE PRIOR ART

The fusion of mouse myeloma cells to spleen cells from immunized mice by Kohler and Milstein in 1975 [*Nature* 256, 495–497 (1975)] demonstrated for the first time that it was possible to obtain a continuous cell line making homogeneous (so-called "monoclonal") antibody. Since this seminal work, much effort has been directed to the production of various hybrid cells (called "hybridomas") and to the use of the antibody made by these hybridomas for various scientific investigations. See, for example, *Current topics in Microbiology and Immunology*, Volume 81 "Lymphocyte Hybridomas", F. Melchers, M. Potter, and N. Warner, Editors, Springer-Verlag, 1978, and references contained therein; C. J. Barnstable, et al., *Cell*, 14, 9–20 (May, 1978); P. Parham and W. F. Bodmer, *Nature* 276, 397–399 (Nov., 1978); *Handbook of Experimental Immunology*, Third Edition, Volume 2, D. M. Wier, Editor, Blackwell, 1978, Chapter 25; and *Chemical and Engineering News*, Jan. 1, 1979, 15–17. These references simultaneously indicate the rewards and complications of attempting to produce monoclonal antibody from hybridomas. While the general technique is well understood conceptually, there are many difficulties met and variations required for each specific case. In fact, there is no assurance, prior to attempting to prepare a given hybridoma, that the desired hybridoma will be obtained, that it will produce antibody if obtained, or that the antibody so produced will have the desired specificity. The degree of success is influenced principally by the type of antigen employed and the selection technique used for isolating the desired hybridoma.

The attempted production of monoclonal antibody to human lymphocyte cell-surface antigens has been reported only in a few instances. See, for example, *Current Topics in Microbiology and Immunology*, ibid, 66–69 and 164–169. The antigens used in these reported experiments were cultured human lymphoblastoid leukemia and human chronic lymphocytic leukemia cell lines. Many hybridomas obtained appeared to produce antibody to various antigens on all human cells. None of the hybridomas produced antibody against a predefined class of human lymphocytes.

It should be understood that there are two principal classes of lymphocytes involved in the immune system of humans and animals. The first of these (the thymus-derived cell or T cell) is differentiated in the thymus from haemopoietic stem cells. While within the thymus, the differentiating cells are termed "thymocytes." The mature T cells emerge from the thymus and circulate between the tissues, lymphatics, and the bloodstream. These T cells form a large proportion of the pool of recirculating small lymphocytes. They have immunological specificity and are directly involved in cell-mediated immune responses (such as graft rejection) as effector cells. Although T cells do not secrete humoral antibodies, they are sometimes required for the secretion of these antibodies by the second class of lymphocytes discussed below. Some types of T cells play a regulating function in other aspects of the immune system.

The mechanism of this process of cell cooperation is not yet completely understood.

The second class of lymphocytes (the bone marrow-derived cells or B cells) are those which secrete antibody. They also develop from haemopoietic stem cells, but their differentiation is not determined by the thymus. In birds, they are differentiated in an organ analogous to the thymus, called the Bursa of Fabricius. In mammals, however, no equivalent organ has been discovered, and it is thought that these B cells differentiate within the bone marrow.

It is now recognized that T cells are divided into at least several subtypes, termed "helper", "suppressor", and "killer" T cells, which have the function of (respectively) promoting a reaction, suppressing a reaction, or killing (lysing) foreign cells. These subclasses are well understood for murine systems, but they have only recently been described for human systems. See, for example, R. L. Evans, et al., *Journal of Experimental Medicine*, Volume 145, 221–232, 1977; and L. Chess and S. F. Schlossman "Functional Analysis of Distinct Human T-Cell Subsets Bearing Unique Differentiation Antigens", in "*Contemporary Topics in Immunobiology*", O. Stutman, Editor, Plenum Press, 1977, Volume 7, 363–379.

The ability of identify or suppress classes or subclasses of T cells is important for diagnosis or treatment of various immunoregulatory disorders or conditions.

For example, certain leukemias and lymphomas have differing prognosis depending on whether they are of B cell or T cell origin. Thus, evaluation of the disease prognosis depends upon distinguishing between these two classes of lymphocytes. See, for example, A. C. Aisenberg and J. C. Long, *The American Journal of Medicine*, 58:300 (March, 1975); D. Belpomme, et al., in "*Immunological Diagnosis of Leukemias and Lymphomas*", S. Thierfelder, et al., eds, Springer, Heidelberg, 1977, 33–45; and D. Belpomme, et al., *British Journal of Haematology*, 1978, 38, 85.

Certain disease states (e.g., juvenile rheumatoid arthritis, malignancies, and agammaglobulinemia) are associated with an imbalance of T cell subclasses. It has been suggested that autoimmune diseases generally are associated with an excess of "helper" T Cells or a deficiency of certain "suppressor" T cells, while agammaglobulinemia is associated with an excess of certain "suppressor" T cells or a deficiency of "helper" T cells. Malignancies generally are associated with an excess of "suppressor" T cells.

In certain leukemias, excess T cells are produced in an arrested stage of development. Diagnosis may thus depend on the ability to detect this imbalance or excess. See, for example, J. Kersey, et al., "Surface Markers Define Human Lymphoid Malignancies with Differing Prognoses" in *Haematology and Blood Transfusion*, Volume 20, Springer-Verlag, 1977, 17–24, and references contained therein.

Acquired agammaglobulinemia, a disease state in which no immune globulin is produced, comprises at least two distinct types. In type I the failure to produce immune globulin is due to an excess of suppressor T cells, while in type II it is due to a lack of helper T cells. In both types, there appears to be no defect or lack in the patients' B cells, the lymphocytes which are responsible for the actual secretion of the antibody; however, these B cells are being either suppressed or "not helped", resulting in greatly decreased or absent immune globulin production. The type of acquired agammaglobulinemia may thus be determined by testing for an excess of suppressor T cells or an absence of helper T cells.

On the therapeutic side, there is some suggestion, as yet not definitely proven, that administration of antibodies against the subtype of T cell in excess may have therapeutic benefit in autoimmune disease or malignancies. For example, a helper T cell cancer (certain cutaneous T cell lymphomas and certain T cell acute lymphoblastic leukemias) may be treated by an antibody to a helper T cell antigen. Treatment of autoimmune disease caused by an excess of helper cells may also be accomplished in the same fashion. Treatment of disease (e.g., malignancies or type I acquired agammaglobulinemia) due to an excess of suppressor T cells may be treated by administration of an antibody to a suppressor T cell antigen.

Antisera against the entire class of human T cells (so-called antihuman thymocyte globulin or ATG) has been reported useful therapeutically in patients receiving organ transplants. Since the cell-mediated immune response (the mechanism whereby transplants are rejected) depends upon T cells, administration of antibody to T cells prevents or retards this rejection process. See, for example, Cosimi, et al., "Randomized Clinical Trial of ATG in Cadaver Renal Allgraft Recipients: Importance of T Cell Monitoring", *Surgery* 40:155–163 (1976) and references contained therein.

The identification and suppression of human T cell classes and subclasses has previously been accomplished by the use of spontaneous autoantibodies or selective antisera for human T cells obtained by immunizing animals with human T cells, bleeding the animals to obtain serum, and adsorbing the antiserum with (for example) autologous but not allogeneic B cells to remove antibodies with unwanted reactivities. The preparation of these antisera is extremely difficult, particularly in the adsorption and purification steps. Even the adsorbed and purified antisera contain many impurities in addition to the desired antibody, for several reasons. First, the serum contains millions of antibody molecules even before the T cell immunization. Second, the immunization causes production of antibodies against a variety of antigens found on all human T cells injected. There is no selective production of antibody against a single antigen. Third, the titer of specific antibody obtained by such methods is usually quite low, (e.g., inactive at dilutions greater than 1:100) and the ratio of specific to non-specific antibody is less than $1/10^6$.

See, for example, the Chess and Schlossman article referenced to above (at pages 365 and following) and the Chemical and Engineering News article referred to above, where the deficiencies of prior art antisera and the advantages of monoclonal antibody are described.

One of the subsets of T cells identified by such prior art antisera has been designated the $TH_2^+$ subset and has been shown to contain both the cytotoxic effector cells for cell-mediated lympholysis and the immunoregulatory suppressor T cells which suppress both T cell and B cell function. This subset contains about 20%–30% of human peripheral T cells. See, for example, articles by E. L. Reinherz, et al., in *J. Immunol.* 123:83(1979) and *New Engl. J. Med.* 300:1061(1979).

SUMMARY OF THE INVENTION

There has now been discovered a novel hybridoma (designated OKT5) which is capable of producing novel monoclonal antibody against an antigen found on normal human peripheral cytotoxic and suppressor $TH_2^+$ T cells (about 20% of normal human peripheral T cells). The antibody so produced is monospecific for a single determinant on normal human cytotoxic and suppressor $TH_2^+$ T cells and contains essentially no other anti-human immune globulin, in contrast to prior art antisera (which are inherently contaminated with antibody reactive to numerous human antigens) and to prior art monoclonal antibodies (which are not monospecific for a human cytotoxic/suppressor T cell antigen). Moreover, this hybridoma can be cultured to produce antibody without the necessity of immunizing and killing animals, followed by the tedious adsorption and purification steps necessary to obtain even the impure antisera of the prior art.

It is accordingly one object of this invention to provide hybridomas which produce antibodies against an antigen found on normal human cytotoxic and suppressor $TH_2^+$ T cells.

It is a further object of the present invention to provide methods for preparing these hybridomas.

A further object of the invention is to provide essentially homogeneous antibody against an antigen found on normal human cytotoxic and suppressor $TH_2^+$ T cells.

A still further object is to provide methods for treatment or diagnosis of disease employing these antibodies.

Other objects and advantages of the invention will become apparent from the examination of the present disclosure.

In satisfaction of the foregoing objects and advantages, there is provided by this invention a novel hybridoma producing novel antibody to an antigen found on normal human cytotoxic and suppressor $TH_2^+$ T cells, the antibody itself, and diagnostic and therapeutic methods employing the antibody. The hybridoma was prepared generally following the method of Milstein and Kohler. Following immunization of mice with normal human thymocytes, the spleen cells of the immunized mice were fused with cells from a mouse myeloma line and the resultant hybridomas screened for those with supernatants containing antibody which gave selective binding to normal E rosette positive human T cells. The desired hybridomas were subsequently cloned and characterized. As a result, a hybridoma was obtained which produces antibody (designated OKT5) against an antigen on normal human cytotoxic and suppressor $TH_2^+$ T cells. Not only does this antibody react with normal human peripheral cytotoxic and suppressor $TH_2^+$ T cells, but it also does not react with other normal peripheral blood lymphoid cells, including helper T cells. In addition, the cell surface antigen recognized by this antibody is detected on approximately 80% of normal human thymocytes.

In view of the difficulties indicated in the prior art and the lack of success reported using malignant cell lines as the antigen, it was surprising that the present method provided the desired hybridoma. It should be emphasized that the unpredictable nature of hybrid cell preparation does not allow one to extrapolate from one antigen or cell system to another. In fact, the present applicants have discovered that using a T cell malignant cell line as the antigen caused formation of hybridomas which did not produce the desired antibody. Attempts to use purified antigens separated from the cell surfaces were also unsuccessful.

Both the subject hybridoma and the antibody produced thereby are identified herein by the designation "OKT5", the particular material referred to being apparent from the context.

The preparation and characterization of the hybridoma and the resultant anitbody will be better understood by reference to the following description and Examples.

DETAILED DESCRIPTION OF THE INVENTION

The method of preparing the hybridoma generally comprises the following steps:

A. Immunizing mice with normal human thyumocytes. While it has been found that female $CAF_1$ mice are preferred, it is contemplated that other mouse strains could be used. The immunization schedule and thymocyte concentration should be such as to produce useful quantities of suitably primed splenocytes. Three immunizations at fourteen day intervals with $2 \times 10^7$ cells/mouse/injection to 0.2 ml phosphate bufffered saline has been found to be effective.

B. Removing the spleens from the immunized mice and making a spleen suspension in an appropriate medium. About one ml of medium per spleen is sufficient. These experimental techniques are well-known.

C. Fusing the suspended spleen cells with mouse myeloma cells from a suitable cell line by the use of a suitable fusion promoter. The preferred ratio is about 5 spleen cells per myeloma cell. A total volume of about 0.5–1.0 ml of fusion medium is appropriate for about $10^8$ splenocytes. Many mouse myeloma cell lines are known and available, generally from members of the academic community or various deposit banks, such as the Salk Institute Cell Distribution Center, La Jolla, Calif. The cell line used should preferably be of the so-called "drug resistant" type, so that unfused myeloma cells will not survive in a selective medium, while hybrids will survive. The most common class is 8-azaguanine resistant cell lines, which lack the enzyme hypoxanthine guanine phophoribosyl transferase and hence will not be supported by HAT (hypoxanthine, aminopterin, and thymidine) medium. It is also generally preferred that the myeloma cell line used be of the so-called "non-secreting" type, in that it does not itself produce any antibody, although secreting types may be used. In certain cases, however, secreting myeloma lines may be preferred. While the preferred fusion promoter is polyethylene glycol having an average molecular weight from about 1000 to about 4000 (commercially available as PEG 1000, etc.), other fusion promoters known in the art may be employed.

D. Diluting and culturing in separate containers, the mixture of unfused spleen cells, unfused myeloma cells, and fused cells in a selective medium which will not support the unfused myeloma cells for a time sufficient to allow death of the unfused cells (about one week). The dilution may be a type of limiting one, in which the volume of diluent is statistically calculated to isolate a certain number of cells (e.g., 1–4) in each separate container (e.g., each well of a microtite plate). The medium is one (e.g., HAT medium) which will not support the drug resistant (e.g., 8-azaguanine resistant) unfused myeloma cell line. Hence, these myeloma cells perish. Since the unfused spleen cells are non-malignant, they have only a finite number of generations. Thus, after a certain period of time (about one week) these unfused spleen cells fail to reproduce. The fused cells, on the other hand, continue to reproduce because they possess the malignant quality of the myeloma parent and the ability to survive in the selective medium of the spleen cell parent.

E. Evaluating the supernatant in each container (well) containing a hybridoma for the presence of antibody to E rosette positive purified human T cells.

F. Selecting (e.g., by limiting dilution) and cloning hybridomas producing the desired antibody.

Once the desired hybridoma has been selected and cloned, the resultant antibody may be produced in one of two ways. The purest monoclonal antibody is produced by in vitro culturing of the desired hybridoma in a suitable medium for a suitable length of time, followed by recovery of the desired antibody from the supernatant. The suitable medium and suitable length of culturing time are known or are readily determined. This in vitro technique produces essentially monospecific monoclonal antibody, essentially free from other specific antihuman immune globulin. There is a small amount of other immune globulin present since the medium contains xenogeneic serum (e.g., fetal calf serum). However, this in vitro method may not produce a sufficient quantity or concentration of antibody for some purposes, since the concentration of monoclonal antibody is only about 50 $\mu$g/ml.

To produce a much greater concentration of slightly less pure monoclonal antibody, the desired hybridoma may be injected into mice, preferably syngenic or semisyngenic mice. The hybridoma will cause formation of antibody-producing tumors after a suitable incubation time, which will result in a high concentration of the desired antibody (about 5–20 mg/ml) in the bloodstream and peritoneal exudate (ascites) of the host mouse. Although these host mice also have normal antibodies in their blood and ascites, the concentration of these normal antibodies is only about 5% of the monoclonal antibody concentration. Moreover, since these normal antibodies are not antihuman in their specificity, the monoclonal antibody obtained from the harvested ascites or from the serum is essentially free of any contaminating antihuman immune globulin. This monoclonal antibody is high titer (active at dilutions of 1:50,000 or higher) and high ratio of specific to non-specific immune globulin (about 1/20). Immune globulin produced incorporating the $\kappa$ light myeloma chains are non-specific, "nonsense" peptides which merely dilute the monoclonal antibody without detracting from its specificity.

EXAMPLE I

Production of Monoclonal Antibodies

A. Immunization and Somatic Cell Hybridization

Female $CAF_1$ mice (Jackson Laboratories; 6–8 weeks old) were immunized intraperitoneally with $2 \times 10^7$ human thymocytes in 0.2 ml of phosphate buffered saline at 14-day intervals. Four days after the third immunization, spleens were removed from the mice, and a single cell suspension was made by pressing the tissue through a stainless steel mesh.

Cell fusion was carried out according to the procedure developed by Kohler and Milstein. $1 \times 10^8$ splenocytes were fused in 0.5 ml of a fusion medium comprising 35% polyethylene glycol (PEG 1000) and 5% dimethylsulfoxide in RPMI 1640 medium (Gibco, Grand Island, N.Y.) with $2 \times 10^7$ P3X63Ag8U1 myeloma cells supplied by Dr. M. Scharff, Albert Einstein College of Medicine, Bronx, N.Y. These myeloma cells secrete IgG$_1$ κ light chains.

B. Selection and Growth of Hybridoma

After cell fusion, cells were cultured in HAT medium (hypoxanthine, aminopterin, and thymidine) at 37° C. with 5% CO$_2$ in a humid atmosphere. Several weeks later, 40 to 100 μl of supernatant from cultures containing hybridomas were added to a pellet of $10^6$ peripheral lymphocytes separated into E rosette positive (E+) and E rosette negative (E−) population, which were prepared from blood of healthy human donors as described by Mendes (*J. Immunol.* 111:860, 1973). Detection of mouse hybridoma antibodies binding to these cells was determined by indirect immunofluorescence. Cells incubated with culture supernatants were stained with a fluorescinated goat-anti-mouse IgG (G/M FITC) Meloy Laboratories, Springield, Va.; F/p=2.5) and the fluorescent antibody-coated cells were subsequently analyzed on the Cytofluorograf FC200/4800A (Ortho Instruments, Westwood, Mass.) as described in Example III. Hybridoma cultures containing antibodies reacting specifically with E+ lymphocytes (T cells) were selected and cloned twice by limiting dilution methods in the presence of feeder cells. Subsequently, the clones were transferred intraperitoneally by injecting $1 \times 10^7$ cells of a given clone (0.2 ml volume) into CAF$_1$ mice primed with 2,6,10,14-tetramethylpentadecane, sold by Aldrich Chemical Company under the name Pristine. The malignant ascites from these mice were then used to characterize lymphocytes as described below in Example II. The subject hybrid antibody OKT5 was demonstrated by standard techniques to be of IgG$_1$ subclass.

EXAMPLE II

Characterization of OKT5 Reactivity

A. Isolation of Lymphocyte Populations

Human peripheral blood mononuclear cells were isolated from healthy volunteer donors (ages 15–40) by Ficoll-Hypaque density gradient centrifugation (Pahrmacia Fine Chemicals, Piscataway, N.J.) following the technique of Boyum, *Scand. J. Clin. Lab. Invest.* 21 (Suppl. 97): 77, 1968. Unfractionated mononuclear cells were separated into surface Ig+ (B) and IG− (T plus Null) populations by Sephadex G-200 anti-F (ab')$_2$ column chromatography as previously described by Chess, et al., *J. Immunol.* 113:1113 (1974). T cells were recovered by E rosetting the IG− population with 5% sheep erythrocytes (Microbiological Associates, Bethesda, MD). The rosetted mixture was layerd over Ficoll-Hypaque and the recovered E+ pellet treated with 0.155M NH$_4$Cl (10 ml per $10^8$ cells). The T cell population so obtained was <2% EAC rosette positive and >95% E rosette positive as determined by standard methods. In addition, the non-rosetting Ig− (Null cell) population was harvested from the Ficoll interface. This latter population was <5% E+ and ≦2% sIg+.

The surface Ig+ (B) population was obtained from the Sephadex G-200 column following elution with normal human gamma globulin as previously described. This population was >95% surface Ig+ and <5% E+.

Normal human macrophages were obtained from the mononuclear population by adherence to polystyrene. Thus, mononuclear cells were resuspended in final culture media (RPMI 1640, 2.5mM HEPES [4-(2-hydroxyethyl)-1-piperazinepropane sulfonic acid] buffer, 0.5% sodium bicarbonate, 200 mM L-glutamine, and 1% penicillin-streptomycin, supplemented with 20% heat-inactivated human AB serum) at a concentration of $2 \times 10^6$ cells and incubated in plastic petri dishes (100×20 mm) (Falcon Tissue Culture Dish; Falcon, Oxnard, Calif.) at 37° C. overnight. After extensive washing to remove non-adherent cells, the adherent population was detached by brisk washing with cold serum-free medium containing 2.5 mM EDTA and occasional scraping with the rubber tip of a disposable syringe plunger. Greater than 85% of the cell population was capable of ingesting latex particles and had morphologic characteristics of monocytes by Wright-Giemsa staining.

B. Isolation of Thymocytes

Normal human thymus gland was obtained from patients aged two months to 14 years undergoing corrective cardiac surgery. Freshly obtained portions of the thymus gland were immediately placed in 5% fetal calf serum in medium 199 (Gibco), finely minced with forceps and scissors, and subsequently made into single cell suspensions by being pressed through wire mesh. The cells were next layered over Ficoll-Hypaque and spun and washed as previously described in section A above. The thymocytes so obtained were >95% viable and ≧90% E rosette positive.

C. Cell Line

An Epstein-Barr Virus (EBV) transformed B cell line from a normal individual (Laz 156) was provided by Dr. H. Lazarus, Sidney Farber Institute, Boston, Mass.

EXAMPLE III

Cytofluorographic Analysis and Cell Separation

Cytofluorographic analysis of monoclonal antibodies with all cell populations was performed by indirect immunofluorescence with fluroescein-conjugated goat anti-mouse IgG (G/M FITC) (Meloy Laboratories) utilizing a Cytofluorograf FC200/4800A (Ortho Instruments). In brief, $1 \times 10^6$ cells were treated with 0.15 ml OKT5 at a 1:500 dilution, incubated at 4° C. for 30 minutes, and washed twice. The cells were then reacted with 0.15 ml of a 1:40 dilution G/M FITC at 4° C. for 30 minutes, centrifuged, and washed three times. Cells were then analyzed on the Cytofluorograf, and the intensity of fluorescence per cell was recorded on a pulse height analyzer. A similar pattern of reactivity was seen at a dilution of 1:10,000, but further dilution caused loss of reactivity. Background staining was obtained by substituting a 0.15 ml aliquot of 1:500 ascites from a CAF$_1$ mouse intraperitoneally injected with a non-producing hybrid clone. Reactivity of lymphoid populations with equine anti-TH$_2$ and normal horse IgG were determined as previously described in the above-referenced Reinherz, et. al., articles.

In experiments designed to separate T cell subsets, $100 \times 10^6$ unfractionated T cells were labeled with 4 ml of a 1:500 dilution of OKT4 or OKT5 and developed with G/M FITC. OKT4 was previously shown to be reactive specifically with 55-60% of peripheral blood T lymphocytes representing the human helper subsets. By utilizing a fluorescence activated cell sorter (FACS-I) (Becton, Dickinson, Mountain View, Calif.), T cells were separated into OKT4+ and OKT4³¹ subsets as well as OKT5+ and OKT5− subsets from the same individual. Post sort viability was <95% by Trypan blue exclusion in all instances. Purity of all separated populations was <95%.

EXAMPLE IV

Analysis of T cell subsets with Equine anti-TH$_2$

In a similar fashion to Example III, equine anti-TH$_2$ was utilized to separate TH$_2$+ and TH$_2$− T cells on FACS by labeling 60×10$^6$ unfractionated T cells with 0.12 ml equine anti-TH$_2$ and 0.1 ml of R/H FITC (Cappel Laboratories, Downington, Pa.) as previously described by Reinherz, et al. Purity and viability of sorted cells were similar to the sorted populations described above. FACS sorted subsets of T cells isolated with equine anti-TH$_2$, OKT4, or OKT5 were placed in culture for 48 hours with RPMI 1640 containing 20% human AB serum, 1% penicillin-streptomycin, 200 mM L-glutamine, 25 mM HEPES buffer (Microbiological Associates), and 0.5% sodium bicarbonate at 37° C. in 5% CO$_2$ humid atmosphere. These cultured cells were then analyzed on the Cytofluorograph as described above. Background staining was determined by substituting normal horse IgG for specific antibody and staining as above.

EXAMPLE V

Functional Studies

A. Proliferative Studies

The mitogenic response to 10$^5$ unseparated and FACS-fractionated T lymphocytes was tested in microculture to optimal doses of Concanavalin A (Con A) (Calbiochem, La Jolla, Calif.) and phyto hemagglutinin (PHA) (Burroughs-Wellcome Company, Greenville, N.C.). Alloantigen proliferative response was measured concurrently for the same populations with mitomycin treated LAZ 156, an EBV transformed human B lymphoblastoid cell line stimulus. Proliferation to tetanus toxoid (Massachusetts Department of Public Health Biological Laboratories, Boston, Mass.) and mumps antigen (Microbiological Associates) were tested utilizing 10 μg/ml final concentration and a 1:20 dilution, respectively. Five percent macrophages obtained in the manner described above were added to all populations at the initiation of in vitro cultures. Mitogen stimulated cultures were pulsed after four days with 0.2 μCi of 3H-thymidine ($^3$H-TdR; 1.9 Ci/mM specific activity) (Schwarz/Mann, Division of Becton, Dickinson, Orangeburg, N.Y.) and harvested 18 hours later on a MASH II apparatus (Microbiological Associates). $^3$H-TdR incorporation was measured on a Packard Scintillation Counter (Packard Instrument Company, Downer's Groove, Ill.). Background $^3$H-TdR incorporation was obtained by subsituting media for mitogen. Soluble and cell surface alloantigen cultures were pulsed after five days with $^3$H-TdR for 18 hours, harvested, and counted as above.

B. Cytotoxicity Studies

Sensitization cultures for cell-mediated lympholysis (CML) were established by placing unfractionated T cells with mitomycin treated stimulator cells, all at 2×10$^6$ cells/ml in multiple microtiter plate wells. At the end of five days, the unfractionated T cells were fractionated into OKT5+ and OKT5− T cells subsets on FACS. These T cell subsets were then added to $^{51}$Cr sodium chromate labeled target cells and specific cytotoxicity determined after a six-hour cell incubation. Percent cytotoxicity was determined with the following formula:

$$\frac{^{51}\text{Cr released by experiment} - ^{51}\text{Cr released spontaneously}}{^{51}\text{Cr released by freeze-thaw} - ^{51}\text{Cr released spontaneously}} \times 100$$

All samples were performed in triplicate and results expressed as the mean ± standard deviation.;

C. Con A Activation of Suppressor Cells and Suppression of MLC

Unfractionated T cells were activated with 20 μg Concanavalin A (Con A) Calbiochem) per 10$^6$ cells. These Con A treated cells were cultured upright in 25 cm$^2$ surface area tissue culture flasks (Falcon, Oxnard, Calif.) in RPMI 1640 (Grand Island Biological Company) containing 20% human AB serum, 1% penicillin-streptomycin, 200 mM L-glutamine, 25 mM HEPES buffer (Microbiological Associates), and 0.5% sodium biacarbonate for 48 hours at 47° C. in a humid atmosphere containing 5% CO$_2$. Untreated control T cells were cultured in an identical fashion but without Con A. Subsequently, cells were spun, washed five times, and added to fresh autologous responder cells in one-way mixed lymphocyte culture (MLC) as described above. In suppression assay, one-way MLCs were established in round-bottom microtiter plates (Linbro Chemical Company, New Haven, Conn.) with triplicate wells, each containing 0.05×10$^6$ responder lymphocytes (whole mononuclear); 0.05×10$^6$ of either unactivated or Con A activated autologous unfractionated or fractionated T cells; and 0.1×10$^6$ mitomycin treated stimulated cells (Laz 156). After five days, cultures were pulsed with 0.2 μCi of $^3$H-TdR and harvested 18 hours later, as above. Percent inhibition of MLC proliferation was then calculated using the formula:

$$\% \text{ inhibition} = \left(1 - \frac{cpm\ Con\ A+}{cpm}\right) \times 100$$

where cpm Con A+ represents the results of $^3$H-TdR incorporation in MLC when Con A activated autologous T cells or T cell subsets are added, and where cpm represents results when unactivated autologous T cells are added.

The production of the hybridoma and the production and characterization of the resulting monoclonal antiboyd were conducted as described in the above Examples. Although large quantities of the subject antibody were prepared by injecting the subject hybridoma intraperitoneally into mice and harvesting the malignant ascites, it is clearly contemplated that the hybridoma could be cultured in vitro by techniques well-known in the art and the antibody removed from the supernatant.

Figure 1:
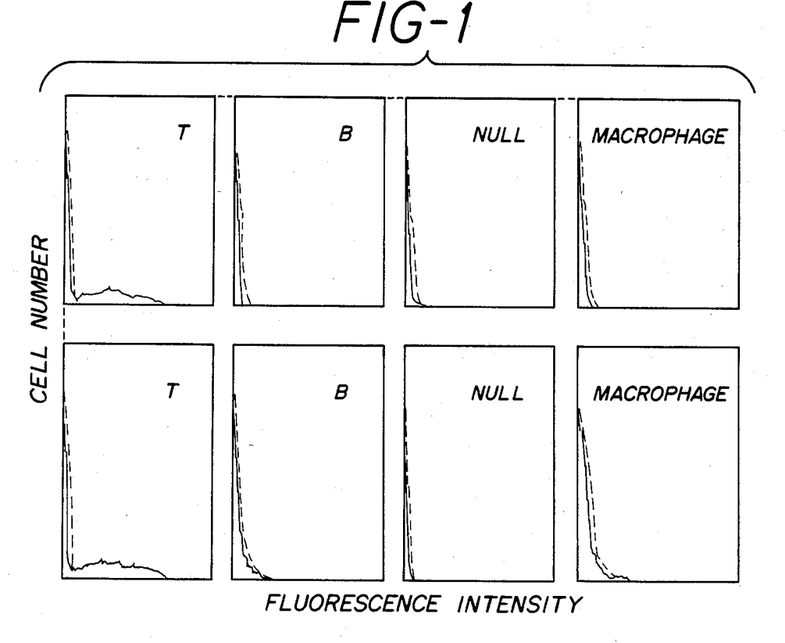
FIG. 1 shows the fluroescence pattern obtained on the Cytofluorograf after reacting normal human peripheral T cells, B cell, Null cells, and macrophages with OKT5 at a 1:1000 dilution and G/M FITC in the upper row. For comparison, results with equine anti-TH$_2$ are shown in the lower row.

As shown in the upper row of FIG. 1, approximately 20% of the human peripheral blood T cells population of a given normal individual is reactive with OKT5, whereas the entire B cell, Null cell, and macrophage populations isolated from the same individual are unreactive with OKT5. Similarly, equine anti-$TH_2$ reacts with 24% of peripheral T cells and is also unreactive with B cells, Null cells and macrophages. The monoclonal antibody is thus characterized in that it is reactive with an antigen contained on the surface of approximately 20% of normal human peripheral T cells, while being unreactive with any antigens on the surface of the other three cell types discussed above. As will be discussed below, the OKT5+ portion of the human peripheral T cell population is included in the cytotoxic and suppressor T cell subset. This differential reactivity is one test by which the subject antibody OKT5 may be detected and distinguished from other antibodies.

Figure 2:
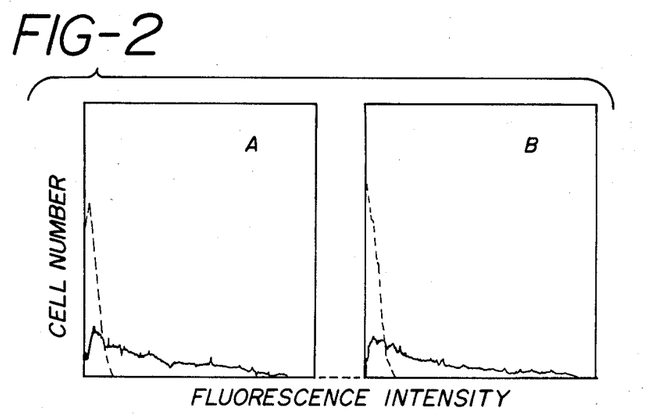
FIG. 2 shows the fluorescence pattern obtained on the Cytofluorgraf after reacting human thymocytes with OKT5 and G/M FITC(A) and with equine anti-TH$_2$(B).

As shown in FIG. 2, approximately 80% of normal human thymocytes from a six-month old infant are reactive with OKT5. Similar results (about 80% reactivity) were obtained using additional thymus specimens from normal individuals two months to 19 years of age. This value is the same as for equine anti-$TH_2$. The pattern of reactivity in FIG. 2 provides a second method of detecting the subject antibody OKT5 and distinguishing it from other antibodies.

Figure 3:
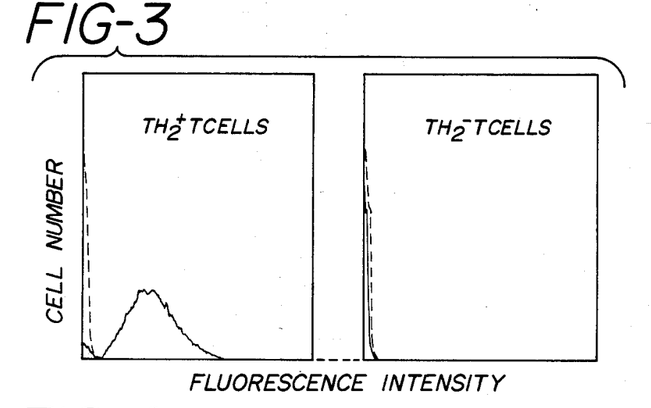
FIG. 3 shows the fluorescence pattern obtained on the Cytofluorograf after reacting equine anti-TH$_2$ separated T cell subsets with OKT5.

As shown in FIG. 3, the subject antibody reacts with $TH_2+$ but not with $TH_2-$ T cells. Approximately 5–10% of the $TH_2+$ subset was unreactive with OKT5. The pattern of reactivity in FIG. 3 provides a third method of detecting the subject antibody OKT5 and distinguishing it from other antibodies.

Figure 4:
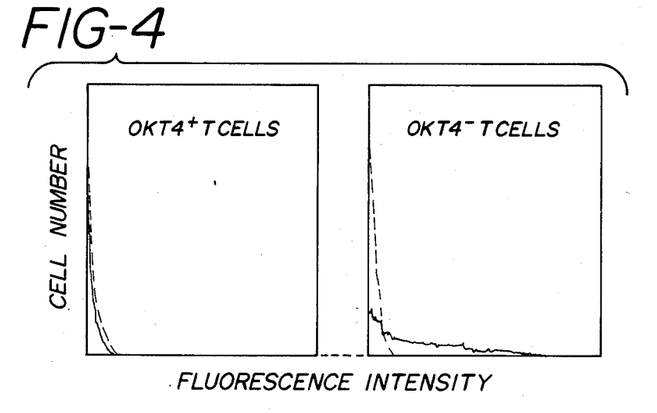
FIG. 4 shows the fluorescence pattern obtained on the Cytofluorograf after reacting OKT4+ separated T cell subsets with OKT5.

As shown in FIG. 4, the OKT4+ T cell subset is entirely unreactive with OKT5. In contrast, the OKT4− T cell subset is largely OKT5+ (6,800 of 10,000 cells tested). These results indicate that the OKT5+ subset of T cells, like the previously defined $TH_2+$ subset, is reciprocal and distinct from the OKT4+ subset. While the OKT4+ subset contains the helper T cells, the OKT5+ subset (like the $TH_2+$ subset) contains cytotoxic and suppressor T cells. This pattern of reactivity in FIG. 4 provides an additional method of identifying OKT5 antibody and distinguishing it from other antibodies.

Figure 5:
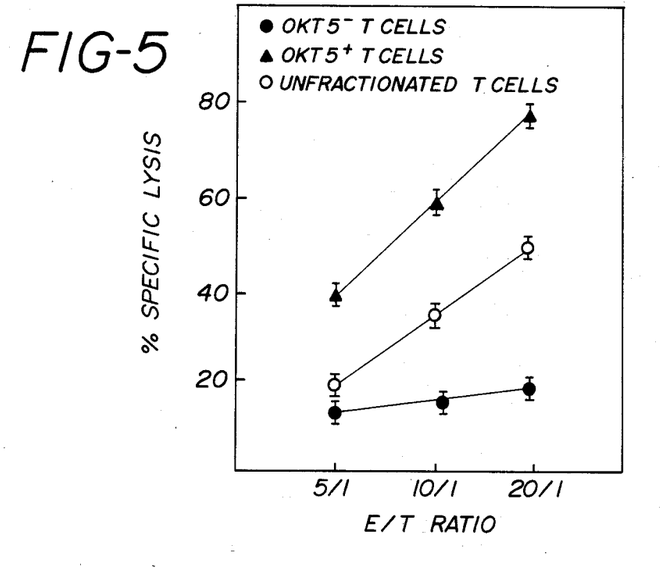
FIG. 5 shows the cytotoxic capacity of unfractionated T cells and T cell subsets separated with OKT5 following allosensitization in MLC.

FIG. 5 shows that the OKT5+ T cell subset effects CML. The degree of lysis mediated by this population is greater than that mediated by the unfractionated T cell population. In contrast, the OKT5− T cell population is minimally lytic. Following activation in MLC against Laz 156, the unfractionated T cells were separated into IKT5+ and OKT5− subsets. Both unfractionated and fractionated T cells were analyzed in CML against $^{51}Cr$ labeled Laz 156 targets at varous effector:target (E:T) ratios. The OKT5+ T cell subsets contained the effector population in cell-mediated lympholysis. At E:T ratios of 5:1, 10:1, and 20:1, the OKT5+ T cell population effected 40%, 58%, and 77% specific lysis, respectively. The lytic capacity of the isolated OKT5+ subset was considerably greater than the unfractionated T cell population. Moreover, the OKT5− T cell population effected significantly less lysis at any E:T ratio tested. Given the earlier observation that the $TH_2+$ T cell subset in man effected CML, the present findings would add support to the notion that the $TH_2+$ and OKT5+ T cell subsets defined similar populations of functionally active T lymphocytes. This differential cytotoxic capacity provides yet another method of identifying OKT5 antibody and distinguising it from other antibodies.

Functional studies were conducted on lymphoid populations which had been separated on a fluorescence activated cell separator (FACS). The results of these studies are shown in Tables I through III below and provide further support for the previously described characterization of the subject monoclonal antibody.

In these studies, an unfractionated T cell population was treated with a 1:500 dilution of OKT5 and G/M FITC and separated on the FACS in OKT5+ and OKT5− subsets. Given the purity of the populations obtained (greater than or equal to 95%), 5% macrophages were added to the separated populations prior to in vitro culture. The unfractionated T cell population and isolated OKT5+ and OKT5− T cell subsets were then stimulated with PHA, Con A, soluble antigens, and alloantigens to access their in vitro proliferative responses.

The proliferative response of the unfractionated T cell populations to PHA and Con A is shown in Table I. A maximal proliferative response by the unfractionated T cell population is obtained with 1 $\mu$g of PHA per $10^6$ cells with diminished responses occurring at 0.5 $\mu$g and 0.1 $\mu$g of PHA per $10^6$ cells. Treatment of the unfractionated T cells with OKT5 and goat-mouse FITC without subsequent fractionation did not alter the proliferative response. In contrast, differences in response to PHA were obtained with the separated OKT5+ and OKT5− T cell subset. The OKT5− population of cells responded to all doses of PHA in a fashion similar to the unseparated T cell population. However, the proliferative response of the OKT5+ cells was significantly less at all doses of PHA tested.

Furthermore, at a dose of PHA of 0.1 $\mu$g per $10^6$ cells, the OKT5+ T cells did not proliferate at all, whereas the OKT5− T cell subset and unfractionated cells were still responsive. The proliferative response of these subsets to Con A, on the other hand, was similar and the two subsets of cells could not be distinguished from one another or the unfractionated T cell population.

The responses to alloantigen in MLC and to soluble antigens were next examined. As shown in Table II, the unfractionated T cell population, the unfractionated T cell population treated with OKT5 and G/M FITC, and both the OKT5+ and OKT5− T cell subsets responded in a similar fashion in MLC against Laz 156. In contrast, proliferative responses to soluble antigens provided the clearest distinction between the subsets. In all cases tested, the OKT5+ T cell subset proliferated minimally to the soluble antigens tetanus toxoid and mumps, whereas the OKT5− T cell subset responded well.

Prior studies demonstrated that the $TH_2^+$ population of T lymphocytes could be induced with Con A to suppress autologous lymphocytes in MLC. To determine whether OKT5+ T cell subset could similarly express suppressor function, T cells were activated for 48 hours with Con A and then sorted with OKT5 and OKT4 monoclonal antibodies into distinct T cell subsets. Subsequently, these separated T cell subpopulations were added to autologous responding lymphocytes at the initiation of MLC. As shown in Table III, unfractionated T cells activated with Con A suppressed autologous cell proliferation in MLC. Treatment with monoclonal antibody and G/M FITC did not alter this result. Although both OKT4+ and OKT5+ T cells proliferated to Con A, only OKT5+ T cells became suppressive when activated with Con A. The OKT4+ subset was not suppressive. In addition, the OKT5 subpopulation, which contains both OKT4+ and OKT4− $TH_2^-$ subpopulations, was minimally suppressive when compared to the highly suppressive OKT5+ population.

Table IV shows the relationship between levels of peripheral T cells and T cell subsets and various disease states. These relationships may be used for diagnostic purposes (e.g., to detect acute infectious mononucleosis) by analyzing the blood sample of an individual suspected of having one of these disease states to determine the levels of T cells and T cell subsets. These relationships may also be used for therapeutic purposes where the cause of the disease state is an elevated level of a T cell subset (e.g., Type I acquired agammaglobulinemia). For therapeutic use, administration of the appropriate monoclonal antibody to a patient with an elevated T cell subset level will decrease or eliminate the excess. The relationships shown in Table IV are a further way in which OKT5 antibody may be detected and distinguished from other antibodies.

Other monoclonal antibody producing hybridomas prepared by the present applicants (designated OKT1, OKT3 and OKT4) are described and claimed in the following U.S. patent applications: Ser. No. 22,132, filed Mar. 20, 1979 now U.S. Pat. No. 4,363,799; Ser. No. 33,639, filed Apr. 26, 1979 now U.S. Pat. No. 4,381,295; and Ser. No. 33,669, filed Apr. 26, 1979 now U.S. Pat. No. 4,361,549. These applications are incorporated herein by reference.

According to the present invention there are provided a hybridoma capable of producing antibody against an antigen found on human cytotoxic and suppressor T cells, a method for producing this hybridoma, monoclonal antibody against an antigen found on human cytotoxic and suppressor T cells, methods for producing the antibody, and methods and compositions for treatment or diagnosis of disease employing this antibody.

TABLE I

MITOGEN RESPONSIVENESS OF UNFRACTIONATED AND OKT5 MONOCLONAL ANTIBODY SEPARATED T CELL SUBSETS

| Proliferative Stimulus | T Cells | T Cells Treated with OKT5 and G/M FITC | OKT5+ Cells | OKT5− Cells |
|---|---|---|---|---|
| PHA (1 μg/$10^6$ cells) | 61,149 ± 6,235 | 54,479 ± 1,003 | 11,419 ± 989 | 58,695 ± 3,228 |
| PHA (0.5 μg/$10^6$ cells) | 48,935 ± 5,699 | 47,101 ± 3,365 | 7,821 ± 1,057 | 51,963 ± 6,811 |
| PHA (0.1 μg/$10^6$ cells) | 19,754 ± 2,177 | 21,681 ± 869 | 839 ± 70 | 25,696 ± 2,782 |
| Con A (250 μg/$10^6$ cells) | 101,771 ± 2,693 | 87,899 ± 9,288 | 94,063 ± 1,651 | 88,269 ± 7,115 |
| Con A (125 μg/$10^6$ cells) | 44,460 ± 2,713 | 47,924 ± 1,056 | 37,709 ± 3,180 | 39,507 ± 4,268 |
| Con A (50 μg/$10^6$ cells) | 38,577 ± 5,169 | 42,605 ± 4,773 | 36,833 ± 3,982 | 40,051 ± 1,666 |
| Media Control | 81 ± 7 | 151 ± 29 | 136 ± 12 | 127 ± 22 |

TABLE II

PROLIFERATIVE RESPONSE OF UNFRACTIONATED TO CELLS AND MONOCLONAL ANTIBODY SEPARATED T CELL SUBSETS TO SOLUBLE ANTIGENS AND ALLOANTIGENS

| Proliferative Stimulus | T Cells | T Cells Treated with OKT5 and G/M FITC | OKT5+ T Cells | OKT5− T cells |
|---|---|---|---|---|
| *Experiment #1* | | | | |
| MLC | 106,547 ± 12,638 | 91,914 ± 2,790 | 116,838 ± 5,707 | 105,636 ± 3,013 |
| Tetanus Toxoid | 21,206 ± 3,656 | 25,782 ± 2,615 | 992 ± 788 | 29,309 ± 2,154 |
| Mumps | 29,300 ± 1,761 | 24,590 ± 3,586 | 1,339 ± 273 | 21,518 ± 3,509 |
| Media | 186 ± 34 | 137 ± 21 | 79 ± 10 | 84 ± 13 |
| *Experiment #2* | | | | |
| MLC | 93,623 ± 2,798 | 92,721 ± 4,623 | 114,822 ± 7,800 | 98,136 ± 5,587 |
| Tetanus Toxoid | 65,328 ± 7,549 | 67,776 ± 10,671 | 1,975 ± 221 | 69,047 ± 7,100 |
| Mumps | 16,591 ± 1,959 | 18,222 ± 2,168 | 322 ± 44 | 37,654 ± 3,176 |
| Media | 64 ± 11 | 79 ± 7 | 58 ± 9 | 61 ± 1 |

TABLE III

OKT5+ T CELLS MEDIATE CON A-INDUCED SUPPRESSION OF MLC

| | Experiment #1 | | Experiment #2 | |
|---|---|---|---|---|
| Cells Added to MLC | $^3$H—Thymidine | % Inhibition | $^3$H—Thymidine | % Inhibition |
| Unfractionated T cells alone | 78,374 ± 4,928 | — | 89,199 ± 10,053 | — |
| (Unfractionated T cells)$_{Con\ A}$ | 21,065 ± 1,716 | 73 | 25,788 ± 3,554 | 71 |

TABLE III-continued
OKT5+ T CELLS MEDIATE CON A-INDUCED SUPPRESSION OF MLC

| | Experiment #1 | | Experiment #2 | |
|---|---|---|---|---|
| Cells Added to MLC | $^3$H—Thymidine | % Inhibition | $^3$H—Thymidine | % Inhibition |
| (Unfractionated T cells) + (monoclonal antibody + G/M FITC)$_{Con\ A}$ | 29,003 ± 2,788 | 63 | 18,393 ± 2,776 | 79 |
| (OKT5$^+$)$_{Con\ A}$ | 14,781 ± 1,236 | 81 | 19,711 ± 875 | 78 |
| (OKT4$^+$)$_{Con\ A}$ | 79,954 ± 4,782 | −2 | 87,629 ± 10,655 | 2 |
| (OKT5$^-$)$_{Con\ A}$ | 67,158 ± 5,839 | 15 | 70,335 ± 8,904 | 21 |

TABLE IV
PERIPHERAL T CELL LEVELS IN DISEASE STATES

| | T Cell Levels | | |
|---|---|---|---|
| Disease State | OKT3$^+$ | OKT4$^+$ | OKT5$^+$ |
| Primary Biliary Cirrhosis (2) | N | + | − |
| Multiple Sclerosis (advanced disease) (8) | − | N | − |
| Myasthemia Gravis (early untreated) (3) | 0 | 0 | 0 |
| Acute Graft vs Host (3) | 0 to − | − | 0 |
| Acquired Agammaglobulinemia | | | |
| Type I | | | + |
| Type II | | 0 | |
| Hyper IgE (4) | − | N | 0 to − |
| Acute Infectious Mononucleosis (4)* | + | 0 to − − | + + |
| Hodgkins Disease | | | |
| Stages I & II | N | N | N |
| Stages III & IV | − − | N | N |

N = within normal limits
0 = absent
+ = above normal
+ + = greatly above normal
− = below normal
− − = greatly below normal
*these levels return to normal about one week prior to the disappearance of clinical symptoms
"The numbers in parentheses indicate the number of patients evaluated."

Although only a single hybridoma producing a single monoclonal antibody against human cytotoxic and suppressor T cell antigen is described, it is contemplated that the present invention encompasses all monoclonal antibodies exhibiting the characteristics described herein. It was determined that the subject antibody OKT5 belongs to the subclass IgG$_1$, which is one of four subclasses of murine IgG. These subclasses of immune globulin G differ from one another in the so-called "fixed" regions, although an antibody to a specific antigen will have a so-called "variable" region which is functionally identical regardless of which subclass of immune globulin G it belongs to. That is, a monoclonal antibody exhibiting the characteristic described herein may be of subclass IgG$_1$, IgG$_2$a, IgG$_2$b, or IgG$_3$, or of classes IgM, IgA, or other known Ig classes. The differences among these classes or subclasses will not affect the selectivity of the reaction pattern of the antibody, but may affect the further reaction of the antibody with other materials, such as (for example) complement or anti-mouse antibodies. Although the subject antibody is specifically IgG$_1$, it is contemplated that antibodies having the patterns of reactivity illustrated herein are included within the subject invention regardless of the immune globulin class or subclass to which they belong.

Further included within the subject invention are methods for preparing the monoclonal antibodies described above employing the hybridoma technique illustrated herein. Although only one example of a hybridoma is given herein, it is contemplated that one skilled in the art could follow the immunization, fusion, and selection methods provided herein and obtain other hybridomas capable of producing antibodies having the reactivity characteristics described herein. Since the individual hybridoma produced from a known mouse myeloma cell line and spleen cells from a known species of mouse cannot be further identified except by reference to the antibody produced by the hybridoma, it is contemplated that all hybridomas producing antibody having the reactivity characteristics described above are included within the subject invention, as are methods for making this antibody employing the hybridoma.

Further aspects of the invention are methods of treatment or diagnosis of disease employing the monoclonal antibody OKT5 or any other monoclonal antibody exhibiting the pattern of reactivity provided herein. The subject antibody may be used to detect excess cytotoxic or suppressor T cell activity by reacting a T cell composition from an individual with OKT5 antibody. Excess cytotoxic or suppressor T cell activity will be indicated by the presence of more than 20–30% of the total peripheral T cell population which reacts with OKT5. This diagnostic technique may be employed using OKT5 antibody alone or in combination with other antibodies (e.g, OKT3 and OKT4) as shown in Table IV. Patterns of reactivity with a panel of antibodies to T cells and T cell subsets will allow more precise detection of certin disease states than is possible using prior diagnostic methods.

Treatment of disease states (e.g., malignancies) manifesting themselves as an excess of suppressive activity may be accomplished by administration of a therapeutically effective amount of OKT5 antibody to an individual in need of such treatment. By selective reaction with suppressor T cell antigen, the effective amount of OKT5 antibody will reduce the excess of suppressor T cells, thus ameliorating the effects of the suppressor T cell excess. Diagnostic and therapeutic compositions comprising effective amounts of OKT5 antibody in admixture with diagnostically or pharmaceutically acceptable carriers, respectively, are also included within the presen invention.

The subject hybridoma OKT5 was deposited in the American Type Culture Collection, 12301 Parklawn Drive, Rockville, Md. 20852 on Sept. 18, 1979, and September 28, 1979, and was given the ATCC accession number CRL 8013 and CRL 8016, respectively.

What is claimed is:

1. Mouse monoclonal antibody that reacts with a same antigen as the monoclonal antibody produced by the hybridoma ATCC CRL 8013 or CRL 8016.

2. The monoclonal antibody of claim 1, wherein the antigen which the antibody reacts with is present on greater than 90% of cytotoxic and suppressor TH$_2$$^+$ T cells, but not on normal human peripheral helper T cells.

3. A monoclonal antibody produced by a hybridoma formed by fusion of cells from a mouse myeloma line and spleen cells from a mouse previously immunized with normal human thymocytes, wherein the monoclonal antibody reacts with a same antigen as the monoclonal antibody produced by the hybridoma ATCC CRL 8013 or CRL 8016.

4. The monoclonal antibody of claim 3, wherein the antigen which the antibody reacts with is present on greater than 90% of normal human peripheral cytotoxic and suppressor $TH_2^+$ T cells, but not on normal human peripheral helper T cells.

* * * * *